US012752072B2

(12) United States Patent
Borrello

(10) Patent No.: US 12,752,072 B2
(45) Date of Patent: Oct. 6, 2026

(54) SYSTEM AND METHOD FOR CONTROLLING VALVE

(71) Applicant: KONINKLIJKE PHILIPS N.V., Eindhoven (NL)

(72) Inventor: Michael Anthony Borrello, Carlsbad, CA (US)

(73) Assignee: Koninklijke Philips N.V., Eindhoven (NL)

( * ) Notice: Subject to any disclaimer, the term of this patent is extended or adjusted under 35 U.S.C. 154(b) by 894 days.

(21) Appl. No.: 18/111,001

(22) Filed: Feb. 17, 2023

(65) Prior Publication Data

US 2023/0393593 A1 Dec. 7, 2023

Related U.S. Application Data

(60) Provisional application No. 63/349,624, filed on Jun. 7, 2022.

(51) Int. Cl.

*A61M 16/20* (2006.01)
*A61M 16/00* (2006.01)
*G05D 7/06* (2006.01)

(52) U.S. Cl.

CPC ........ *A61M 16/205* (2014.02); *A61M 16/024* (2017.08); *G05D 7/0635* (2013.01);

(Continued)

(58) Field of Classification Search

CPC . G05D 7/0623; G05D 7/0635; A61M 16/205; A61M 2016/0027;

(Continued)

(56) References Cited

U.S. PATENT DOCUMENTS 5,072,729 A 12/1991 Devries
5,127,400 A 7/1992 Devries (Continued)

FOREIGN PATENT DOCUMENTS

WO 2015200878 A1 12/2015

OTHER PUBLICATIONS

Mahajan, R.P. et al., "Relationship between expired lung volume, peak flow rate and peak velocity time during a voluntary cough Manoeuvre", British Journal of Anaesthesia 1994; 72: 298-301.

(Continued)

*Primary Examiner* — Kendra D Carter
*Assistant Examiner* — Keira Eileen Callison
(74) *Attorney, Agent, or Firm* — Daniel H. Brean

(57) ABSTRACT

A system for controlling a valve disposed in fluid communication with a fluid circuit is provided. The system includes a flow sensor configured to determine a measured flow and a pressure sensor configured to determine a measured pressure of fluid flowing from the fluid circuit to the valve. The system includes an adaptive controller configured to determine a desired flow based at least on the measured pressure, the measured flow, and a target pressure; determine a flow error as a difference between the desired flow and the measured flow; and determine a desired position of the valve based on the flow error, such that the flow error is reduced. The system includes a position controller configured to determine an actuating electric parameter based at least on the desired position and a valve actuator configured to apply an actuating force on the valve based at least on the actuating electric parameter.

20 Claims, 8 Drawing Sheets

(52) U.S. Cl.
CPC ............... *A61M 2016/0027* (2013.01); *A61M 2016/0042* (2013.01); *A61M 2205/3331* (2013.01); *A61M 2205/3334* (2013.01)

(58) Field of Classification Search
CPC ...... A61M 2016/0042; A61M 16/0066; A61M 16/1055; A61M 16/1065; A61M 16/107; A61M 16/1095; A61M 16/204; A61M 2016/0015; A61M 2205/0244; A61M 2205/0294; A61M 2205/103; A61M 2205/106; A61M 2205/11; A61M 2205/3317; A61M 2205/3375; A61M 2205/7518; A61M 16/024; A61M 16/0883; A61M 16/12; A61M 16/20; A61M 2202/0208; A61M 2205/15; A61M 2205/3331; A61M 2205/3334; A61M 2205/50; A61M 2230/46; A61M 16/206
See application file for complete search history.

(56) References Cited

U.S. PATENT DOCUMENTS

| | | | | |
|---|---|---|---|---|
| 5,331,995 | A * | 7/1994 | Westfall | A61M 16/209 137/487 |
| 5,339,807 | A | 8/1994 | Carter | |
| 5,632,270 | A | 5/1997 | O'Mahony | |
| 5,771,884 | A | 6/1998 | Yarnall | |
| 5,813,399 | A | 9/1998 | Isaza | |
| 6,148,816 | A | 11/2000 | Heinonen | |
| 6,192,885 | B1 | 2/2001 | Jalde | |
| 6,564,798 | B1 | 5/2003 | Jalde | |
| 8,439,036 | B2 | 5/2013 | Winter | |
| 8,469,030 | B2 | 6/2013 | Winter | |
| 8,469,031 | B2 | 6/2013 | Winter | |
| 9,144,658 | B2 | 9/2015 | Li | |
| 9,433,743 | B2 | 9/2016 | Williams | |
| 9,931,058 | B2 | 4/2018 | Hyohgo | |
| 9,962,514 | B2 | 5/2018 | Williams | |
| 9,962,515 | B2 | 5/2018 | Williams | |
| 9,987,457 | B2 | 6/2018 | Winter | |
| 10,753,487 | B2 | 8/2020 | Wojick | |
| 10,828,657 | B2 | 11/2020 | Heinonen | |
| 2021/0262582 | A1 | 8/2021 | Yost | |
| 2021/0290883 | A1 * | 9/2021 | Dong | A61M 16/00 |

OTHER PUBLICATIONS

Bianchi, C. et al., "Cough Peak Flows: Standard Values for Children and Adolescents", American Journal of Physical Medicine & Rehabilitation, Jun. 2008. Abstract.

Andersen, B. L. et al., "The Analysis and Design of Pneumatic Systems", Krieger Publishing, Florida 1967. Review.

* cited by examiner

SYSTEM AND METHOD FOR CONTROLLING VALVE

CROSS-REFERENCE TO RELATED APPLICATIONS

This patent application claims the priority benefit under 35 U.S.C. § 119(e) of U.S. Provisional Application No. 63/349,624, filed on Jun. 7, 2022, the contents of which are herein incorporated by reference.

TECHNICAL FIELD

The present disclosure relates generally to systems and methods for controlling a valve disposed in fluid communication with a fluid circuit. The present disclosure further relates to a valve system including the valve and a ventilator including the valve system.

BACKGROUND

Typically, control units for valves disposed in fluid communication with a fluid circuit use force control. Precise control of such force-controlled valves may present a significant challenge, especially when the valves are expected to precisely follow an arbitrary pressure trajectory, for example positive end expiratory pressure (PEEP) over time, or when the pressure trajectory has rapid acceleration over different ranges of flow. This is because these valves may be easily affected by disturbance forces, such as actuator shaft-bearing friction and/or stiction. These valves are further affected by disturbance forces due to sudden pressure events, such as coughs. Thereby, the disturbance forces may negatively affect accuracy and precision in following or tracking the pressure trajectory over time. The disturbance forces may further result in a variety of undesirable responses including overshoot, slow convergence, valve fluttering, and valve chattering. Further, the disturbance forces may lead to oscillatory perturbations. In some cases, the oscillatory perturbations may cause false breath triggering or blocked triggering. For example, overshoot during initial exhalation transient may cause false breath triggering. To avoid chattering and oscillatory perturbations, the valves may be overdamped. Thus, the valves may respond slowly to current control signals. This may slow the valve and may create further issues for following the pressure trajectory.

Moreover, such systems may passively respond to overpressure (e.g., due to a cough) in the fluid circuit. In some examples, such systems may result in-breath loss of PEEP (for cough events). Further, to accommodate the wide range of load dynamics, the control units may require extremely complex ad-hoc control methods that are not easily predictable or maintained. In some cases, the ad-hoc control methods may not have stability and may defy analytic methods of determining global stability. Given these difficulties, designers may resort to other ad-hoc methods that rely on pre-use calibrations of the valves and/or dominant feedforward (open loop) control to avoid the side effects of strong feedback control. Thus, the control units may not be robust.

Furthermore, the relation between pressure and flow is nonlinear and the load dynamics may vary significantly between different patients and within the breath itself. Specifically, changes in the pressure are often proportional to the square of the flow through a restriction. Therefore, there may be dynamic variation between the different patients, and within the breath for any one patient due to an instantaneous magnitude of the pressure and the flow. This may cause linear controls to be ineffective in providing adequate pressure control across all different patients. For example, lung time constant alone may have several orders of magnitude difference when considering the different patients, such as neonatal patients and adult patients, and all their possible pathologies. Effective controls for nonlinear systems may require well-structured complex methods and may be based on systematically proven principles rather than the ad-hoc methods.

In addition, actuator mechanisms of the valves typically provide a unidirectional actuator force and thus the valves cannot be actively retracted. In other words, the actuator mechanisms of the valves "push" the valves to a closed state. The actuator mechanisms may open the valves to an open state, to release flow, by lowering an actuator current, but not reversing the actuator current direction. Lowering the actuator current may unbalance a closing force (i.e., the actuator force) and may allow any back pressure (such as overpressure due to cough) on the valves to passively force the valves to the open state, independent of the closing force. Thus, the systems may not have an ability to provide feedback control when more flow is required to reduce pressure (e.g., in case of the overpressure). Further, controlling pressure may be challenging during the start of exhalation.

In control units using the force control, actuator mechanism/valve contact occurs only when the actuator force is greater than a pressure force. In some cases, the actuator mechanisms may be designed to apply a bidirectional force (retraction as well as push). However, rapid retraction may cause separation between the actuator mechanisms and the valves due to passive valve inertia. Thus, the valves may mechanically decouple or separate from their actuator mechanisms. This separation may effectively 'open' the control loop, i.e., the valves may no longer be under control of the actuator mechanisms. This may further make controlling pressure challenging during the transients.

SUMMARY

Accordingly, one or more aspects of the present disclosure relate to a system for controlling a valve disposed in fluid communication with a fluid circuit. The system includes a flow sensor configured to determine a measured flow of fluid flowing from the fluid circuit to the valve. The system further includes a pressure sensor configured to determine a measured pressure of fluid flowing from the fluid circuit to the valve. The system further includes an adaptive controller communicably coupled to the flow sensor and the pressure sensor. The adaptive controller is configured to receive signals indicative of a target pressure, the measured flow, and the measured pressure. The adaptive controller is further configured to determine a desired flow based at least on the measured pressure, the measured flow, and the target pressure. The adaptive controller is further configured to determine a flow error as a difference between the desired flow and the measured flow. The adaptive controller is further configured to determine a desired position of the valve based on the flow error, such that the flow error is reduced. The system further includes a position controller communicably coupled to the adaptive controller. The position controller is configured to determine an actuating electric parameter based at least on the desired position of the valve. The system further includes a valve actuator communicably coupled to the position controller and the valve. The valve actuator is configured to apply an actuating force on the valve based at least on the actuating electric parameter.

Another aspect of the present disclosure relates to a method for controlling a valve disposed in fluid communication with a fluid circuit. The method includes determining a measured flow of fluid flowing from the fluid circuit to the valve. The method further includes determining a measured pressure of fluid flowing from the fluid circuit to the valve. The method further includes determining a desired flow based at least on the measured pressure, the measured flow, and a target pressure. The method further includes determining a flow error as a difference between the desired flow and the measured flow. The method further includes determining a desired position of the valve based on the flow error, such that the flow error is reduced. The method further includes determining an actuating electric parameter based at least on the desired position of the valve. The method further includes applying an actuating force on the valve based at least on the actuating electric parameter.

Another aspect of the present disclosure relates to a valve system for use with a fluid circuit. The valve system includes a valve, a flow sensor, a pressure sensor, an adaptive controller, a position controller, and a valve actuator. The valve includes a valve housing defining an inlet port disposed in fluid communication with the fluid circuit and an exhaust port disposed in fluid communication with an environment external to the valve. The valve further includes a valve body at least partially received within the valve housing and movable relative to the valve housing. The valve body is configured to control fluid flow between the inlet port and the exhaust port. The flow sensor is configured to determine a measured flow of fluid flowing from the fluid circuit to the inlet port of the valve. The pressure sensor is configured to determine a measured pressure of fluid flowing from the fluid circuit to the inlet port of the valve. The adaptive controller is communicably coupled to the flow sensor and the pressure sensor. The adaptive controller is configured to receive signals indicative of a target pressure, the measured flow, and the measured pressure. The adaptive controller is further configured to determine a desired flow based at least on the measured pressure, the measured flow, and the target pressure. The adaptive controller is further configured to determine a flow error as a difference between the desired flow and the measured flow. The adaptive controller is further configured to determine a desired position of the valve body based on the flow error, such that the flow error is reduced. The position controller is communicably coupled to the adaptive controller. The position controller is configured to determine an actuating electric parameter based at least on the desired position of the valve body. The valve actuator is communicably coupled to the position controller. The valve actuator is configured to apply an actuating force on the valve body based at least on the actuating electric parameter in order to control fluid flow from the inlet port to the exhaust port.

Another aspect of the present disclosure relates to a ventilator for use with a patient. The ventilator includes a patient circuit including an inspiratory limb configured to supply breathable gas to the patient and an expiratory limb configured to receive exhaled gas from the patient. The ventilator further includes the valve system of the previous aspect. The inlet port of the valve is disposed in fluid communication with the expiratory limb of the patient circuit and the valve is configured to discharge the exhaled gas to the environment external to the valve.

A general object of the disclosure is to provide systems and methods for precise and accurate control of a valve disposed in fluid communication with a fluid circuit, such as a patient circuit. Specifically, the system enables an accurate tracking of a specified pressure trajectory signal to control the valve precisely and accurately.

Another object of the disclosure is to provide a valve system for use with the fluid circuit including the system and the valve, such that the system provides precise and accurate control of the valve.

Yet another object of the disclosure is to provide a ventilator for use with a patient including the patient circuit and the valve system.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

BRIEF DESCRIPTION OF THE DRAWINGS

Exemplary embodiments disclosed herein may be more completely understood in consideration of the following detailed description in connection with the following figures. The figures are not necessarily drawn to scale. Like numbers used in the figures refer to like components. However, it will be understood that the use of a number to refer to a component in a given figure is not intended to limit the component in another figure labeled with the same number.

DETAILED DESCRIPTION

Figure 1:
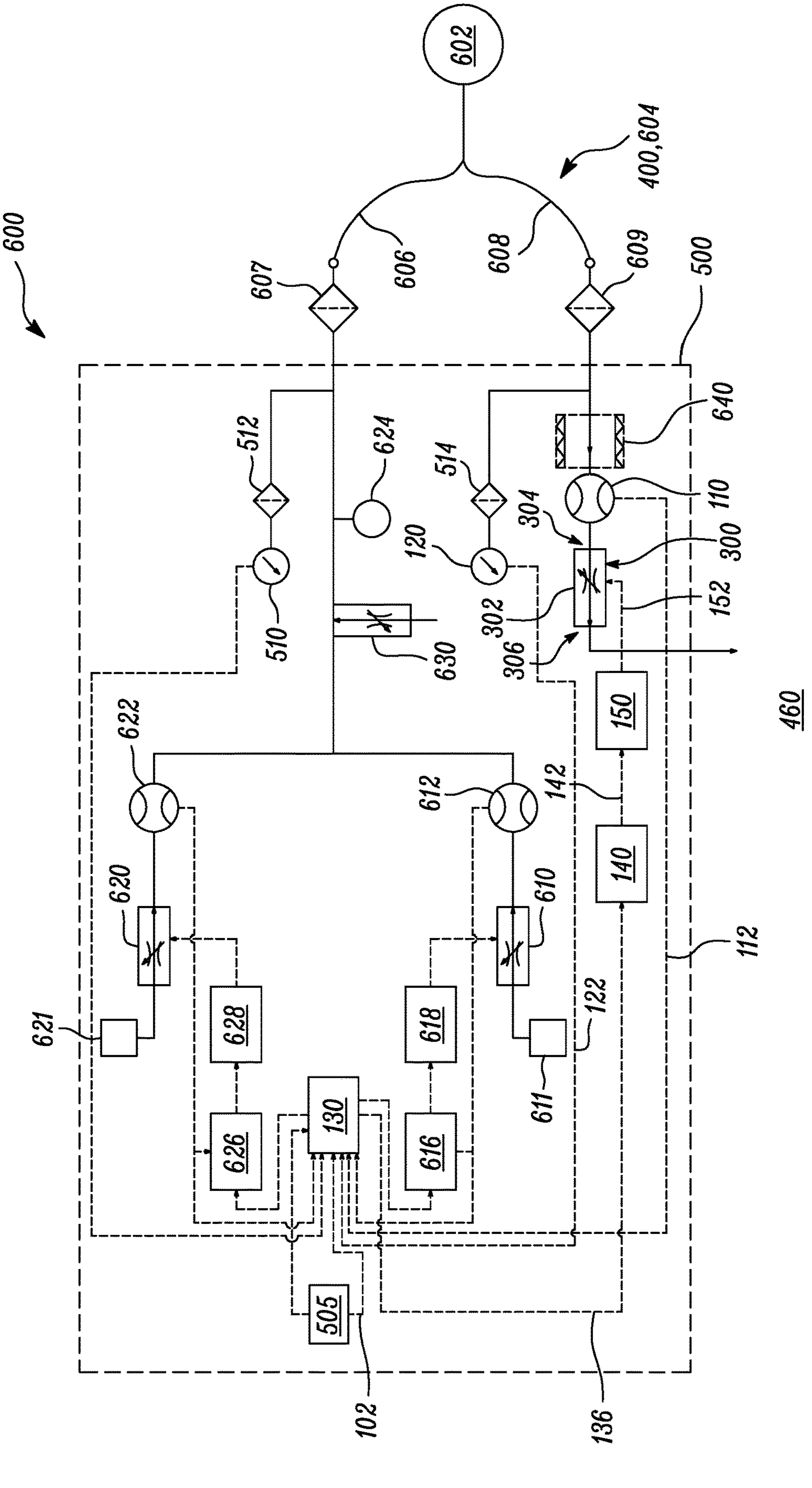
FIG. 1 is a schematic block diagram of a ventilator for use with a patient, according to an embodiment of the present disclosure.

In the following description, reference is made to the accompanying figures that form a part thereof and in which various embodiments are shown by way of illustration. It is to be understood that other embodiments are contemplated and may be made without departing from the scope or spirit of the present disclosure. The following detailed description, therefore, is not to be taken in a limiting sense.

As used herein, the singular form of "a", "an", and "the" include plural references unless the context clearly dictates otherwise.

As used herein, the terms "first" and "second" are used as identifiers. Therefore, such terms should not be construed as limiting of this disclosure. The terms "first" and "second" when used in conjunction with a feature or an element can be interchanged throughout the embodiments of this disclosure.

As used herein, "at least one of A and B" should be understood to mean "only A, only B, or both A and B".

As used herein, the term "controller" refers to a programmable analog and/or digital devices (including an associated memory part or portion) that can store, retrieve, execute and process data (e.g., software routines and/or information used by such routines), including, without limitation, a field programmable gate array (FPGA), a complex programmable logic device (CPLD), a programmable system on a chip (PSOC), an application specific integrated circuit (ASIC), a microprocessor, a microcontroller, a programmable logic controller, or any other suitable processing device or apparatus. The memory portion can be any one or more of a variety of types of internal and/or external storage media such as, without limitation, RAM, ROM, EPROM(s), EEPROM(s), FLASH, and the like that provide a storage register, i.e., a non-transitory machine readable medium, for data and program code storage such as in the fashion of an internal storage area of a computer and can be volatile memory or nonvolatile memory.

As used herein, the terms "communicably coupled to" and "communicably connected to" refers to direct coupling between components and/or indirect coupling between components via one or more intervening components. Such components and intervening components may comprise, but are not limited to, junctions, communication paths, components, circuit elements, circuits, functional blocks, and/or devices. As an example of indirect coupling, a signal conveyed from a first component to a second component may be modified by one or more intervening components by modifying the form, nature, or format of information in a signal, while one or more elements of the information in the signal are nevertheless conveyed in a manner that can be recognized by the second component.

As used herein, s' is a LaPlace operator modeling a linear, continuous time, physical system. $s=\sigma+j\omega$, where $\omega$ is a frequency of the complex plane and $\sigma$ is a real component.

As used herein, 'z' is a discrete time operator. An inverse of z is the one step unit delay operator.

Although methods and systems described below are described in connection with precision flow control of breathable gas in ventilators, the methods and the systems could be applied to virtually any application requiring precision 'back pressure tracking' in the presence of varying loads and disturbances.

FIG. 1 illustrates a ventilator 600 for use with a patient 602 according to an embodiment of the present disclosure. Ventilator 600 includes a patient circuit 604 and a valve system 500 for use with a fluid circuit 400. In the illustrated embodiment of FIG. 1, fluid circuit 400 is patient circuit 604. However, in some other embodiments, fluid circuit 400 can be any circuit including one or more discrete components that transport or are in a communication with any fluid.

Ventilator 600 may be structured to supply breathable gas, such as air, oxygen, or a combination thereof, to an airway of patient 602 to augment or substitute for respiratory effort of patient 602. Ventilator 600 may be operated in a variety of modes depending upon the particular needs of patient 602.

Patient circuit 604 includes an inspiratory limb 606 configured to supply breathable gas to patient 602. Patient circuit 604 further includes an expiratory limb 608 configured to receive exhaled gas from patient 602. Therefore, ventilator 600 employs a dual-limb patient circuit and may be used in life support situations.

Valve system 500 includes a valve 300. Valve 300 includes a valve housing 302 defining an inlet port 304 disposed in fluid communication with fluid circuit 400 and an exhaust port 306 disposed in fluid communication with an environment 460 external to valve 300. In some embodiments, valve 300 is an exhalation valve. In some embodiments, valve 300 may be any exit valve or relief valve used in back pressure tracking applications.

As schematically shown in FIG. 1, inlet port 304 of valve 300 is disposed in fluid communication with expiratory limb 608 of patient circuit 604. Valve 300 is configured to discharge the exhaled gas to environment 460 external to valve 300. Valve 300 may actively control exhaustion of the exhaled gas from patient 602 to environment 460.

In some embodiments, ventilator 600 further includes an air valve 610, an oxygen valve 620, and a safety valve 630. In the illustrated embodiment of FIG. 1, valve system 500 includes air valve 610, oxygen valve 620, and safety valve 630. Air valve 610 is configured to control an air flow of air from an air source 611, such as a blower, to inspiratory limb 606. Similarly, oxygen valve 620 is configured to control an oxygen flow of oxygen from an oxygen source 621 to inspiratory limb 606.

During exhalation, the exhaled gas from patient 602 flows through expiratory limb 608 of patient circuit 604 and inspiratory limb 606 is blocked. This is because during exhalation, air valve 610, oxygen valve 620, and safety valve 630 are closed.

In some embodiments, ventilator 600 further includes an exhalation filter 609. The exhaled gas flows from expiratory limb 608 of patient circuit 604 through exhalation filter 609 to prevent bacterial contamination at inlet port 304 of valve 300.

In some embodiments, ventilator 600 may further include an inhalation filter 607. The breathable gas flows from inhalation filter 607 to inspiratory limb 606 of patient circuit 604. Inhalation filter 607 may any prevent bacterial contamination from the breathable gas to patient 602.

In some embodiments, ventilator 600 may further include a heater 640. In the illustrated embodiment of FIG. 1, valve system 500 includes heater 640. The exhaled gas flows from expiratory limb 608 of patient circuit 604 through heater 640. Heater 640 may heat the exhaled gas to raise temperature of the exhaled gas to avoid condensation of water vapor on any downstream components of valve system 500.

Valve system 500 further includes a flow sensor 110, a pressure sensor 120, an adaptive controller 130 communicably coupled to flow sensor 110 and pressure sensor 120, a position controller 140 communicably coupled to adaptive controller 130, and a valve actuator 150 communicably coupled to position controller 140.

In some embodiments, ventilator 600 further includes an air flow sensor 612 and an oxygen flow sensor 622. In the illustrated embodiment of FIG. 1, valve system 500 includes air flow sensor 612 and oxygen flow sensor 622. Air flow sensor 612 may be configured to measure the air flow from air valve 610 to inspiratory limb 606. Similarly, oxygen flow sensor 622 may be configured to measure the oxygen flow from oxygen valve 620 to inspiratory limb 606.

In some embodiments, the air flowing through air valve 610 and the oxygen flowing through oxygen valve 620 are mixed to form the breathable gas. In some embodiments, ventilator 600 further includes an oxygen sensor 624 configured to measure an amount of the oxygen in the breathable gas. Oxygen sensor 624 may be configured to detect an oxygen leak.

In some embodiments, valve system 500 further includes an inhalation pressure sensor 510 configured to measure pressure of the breathable gas flowing to inspiratory limb 606. In some embodiments, valve system 500 may further include an additional filter 512 configured to prevent condensation and contamination from the breathable gas to patient 602.

Flow sensor 110 is configured to determine a measured flow of fluid flowing from fluid circuit 400 to valve 300. Specifically, flow sensor 110 is configured to determine the measured flow of fluid flowing from expiratory limb 608 of fluid circuit 400 to inlet port 304 of valve 300. In some embodiments, flow sensor 110 is configured to generate a signal 112 indicative of the measured flow determined by flow sensor 110. Flow sensor 110 can be any hardware sensor known in the art. For example, flow sensor 110 may include a micro-electro-mechanical system (MEMS) type flow sensor, an ultrasound transducer, a Doppler flow sensor, or any other suitable flow sensor.

Pressure sensor 120 is configured to determine a measured pressure of fluid flowing from fluid circuit 400 to valve 300. Specifically, pressure sensor 120 is configured to determine the measured pressure of fluid flowing from expiratory limb 608 of fluid circuit 400 to inlet port 304 of valve 300. In some embodiments, pressure sensor 120 is configured to generate a signal 122 indicative of the measured pressure determined by pressure sensor 120. Pressure sensor 120 can be any hardware sensor known in the art. For example, pressure sensor 120 may include a capacitive sensor, a piezoresistive pressure transducer, a fiber optic pressure sensor, or any other suitable pressure sensor. In some embodiments, valve system 500 may further include an additional filter 514 configured to prevent condensation and contamination from the exhaled gas to pressure sensor 120.

A signal 102 is further indicative of a target pressure. Adaptive controller 130 is configured to receive signals 102, 112, 122 indicative of the target pressure, the measured flow, and the measured pressure, respectively. In some embodiments, valve system 500 may include a memory 505 communicably coupled to adaptive controller 130. In some embodiments, memory 505 may be configured to store the target pressure. Adaptive controller 130 may retrieve the target pressure from memory 505 via signal 102. In some embodiments, memory 505 may include a read only memory (ROM), electronically programmable ROM (EPROM), flash memory, solid state drive (SSD), or other electronic storage medium; or a magnetic disk or other magnetic storage medium. In some embodiments, memory 505 may further store other ventilator parameters or settings, such as the ventilation mode (e.g., pressure support ventilation mode or PSV mode), parameters of that ventilation mode (e.g., support pressure setting of the PSV mode), and so forth. In some embodiments, the target pressure may provide an expiratory retard. The expiratory retard may provide the user with a tool to balance the expiratory work of breathing and oxygenation. In some embodiments, pressure fall time of the target pressure may be adjusted for therapeutic benefits. For example, rapid release of exhaled flow may minimize expiratory work of breathing and extended fall (the expiratory retard) may optimize oxygenation.

Signal 102 indicative of the target pressure may be a specified pressure trajectory signal, such as positive end expiratory pressure (PEEP). In some embodiments, the pressure trajectory signal may be specified by a user as appropriate for a therapy of patient 602.

The PEEP may help to recruit collapsed air spaces in the lung and maintain the recruited volume during the process of ventilating the lung through a breath cycle. Valve 300 may enable PEEP control. Valve 300 may initially open to allow exhaustion of the exhaled gas, however, may retard the exhaustion of the exhaled gas towards the end of the exhalation to maintain pressure in patient circuit 604 and likewise lung pressure to the PEEP. For either 'supported' or 'mandatory' breaths, ventilator 600 may leave pressure in patient circuit 604 and the lung pressure at the end of inhalation above the PEEP. Another function of valve 300 may be to provide a stable and predictable transition from the end inhalation pressure to the PEEP. This may have therapeutic benefits or deleterious effects.

At the start of exhalation, valve 300 should 'get out of the way' as exhaustion of the exhaled gas occurs allowing the natural elastic recoil of the lungs to expel gas. Too much delay in reaching the PEEP may trap residual volume in the lungs before the next breath is initiated. This may lead to 'intrinsic' PEEP (aka Auto-PEEP) or if patient 602 is actively attempting to exhale, impose excessive expiratory work of breathing on patient 602. Likewise, if valve 300 does not sufficiently retard the flow, the pressure of patient circuit 604 may fall below the PEEP, and if not recovered quickly enough, may cause atelectasis (collapse of lung alveoli). Typically, controls that can strike this balance are difficult to achieve since the dynamics imposed by lung mechanics vary not only from patient to patient but within the breath itself.

Adaptive controller 130 is configured to determine a desired position of valve 300. In some embodiments, adaptive controller 130 is configured to generate a signal 136 indicative of the desired position of valve 300. In some embodiments, the desired position is the desired valve stroke of valve 300.

Further, position controller 140 is configured to determine an actuating electric parameter based at least on the desired position of valve 300. In some embodiments, position controller 140 is configured to receive at least signal 136 indicative of the desired position of valve 300 and determine the actuating electric parameter based at least on the desired position of valve 300. In some embodiments, position controller 140 is configured to generate a signal 142 indicative of the actuating electric parameter. In other words, position controller 140 is configured to generate signal 142 indicative of the actuating electric parameter based at least on signal 136 indicative of the desired position of valve 300.

Further, valve actuator 150 is configured to apply an actuating force 152 on valve 300 based at least on the actuating electric parameter. In some embodiments, valve actuator 150 is configured to receive at least signal 142 indicative of the actuating electric parameter and apply actuating force 152 on valve 300 based at least on the actuating electric parameter. Valve actuator 150 is configured to apply actuating force 152 on valve 300 in order to control fluid flow from inlet port 304 to exhaust port 306. Thus, actuating electric parameter essentially determines the fluid flow. Further, valve actuator 150 may apply actuating force 152 on valve 300 in either direction depending on the actuating electric parameter. Thus, valve actuator 150 may provide symmetric pushing and pulling forces on valve 300 such that a valve flow area can be increased and decreased according to the actuating electric parameter.

Flow sensor 110, pressure sensor 120, adaptive controller 130, position controller 140, and valve actuator 150 will be described in more detail below.

In some embodiments, ventilator 600 may further include an air flow controller 616 configured to control air valve 610 and an air valve actuator 618 configured to actuate air valve 610. Similarly, in some embodiments, ventilator 600 may further include an oxygen flow controller 626 configured to control oxygen valve 620 and an oxygen valve actuator 628 configured to actuate oxygen valve 620.

Ventilator 600 may include additional components (for example, housings, seals, fluid conduits, electric cables, etc.) that are not shown in FIG. 1 for the purpose of clarity.

Figure 2:
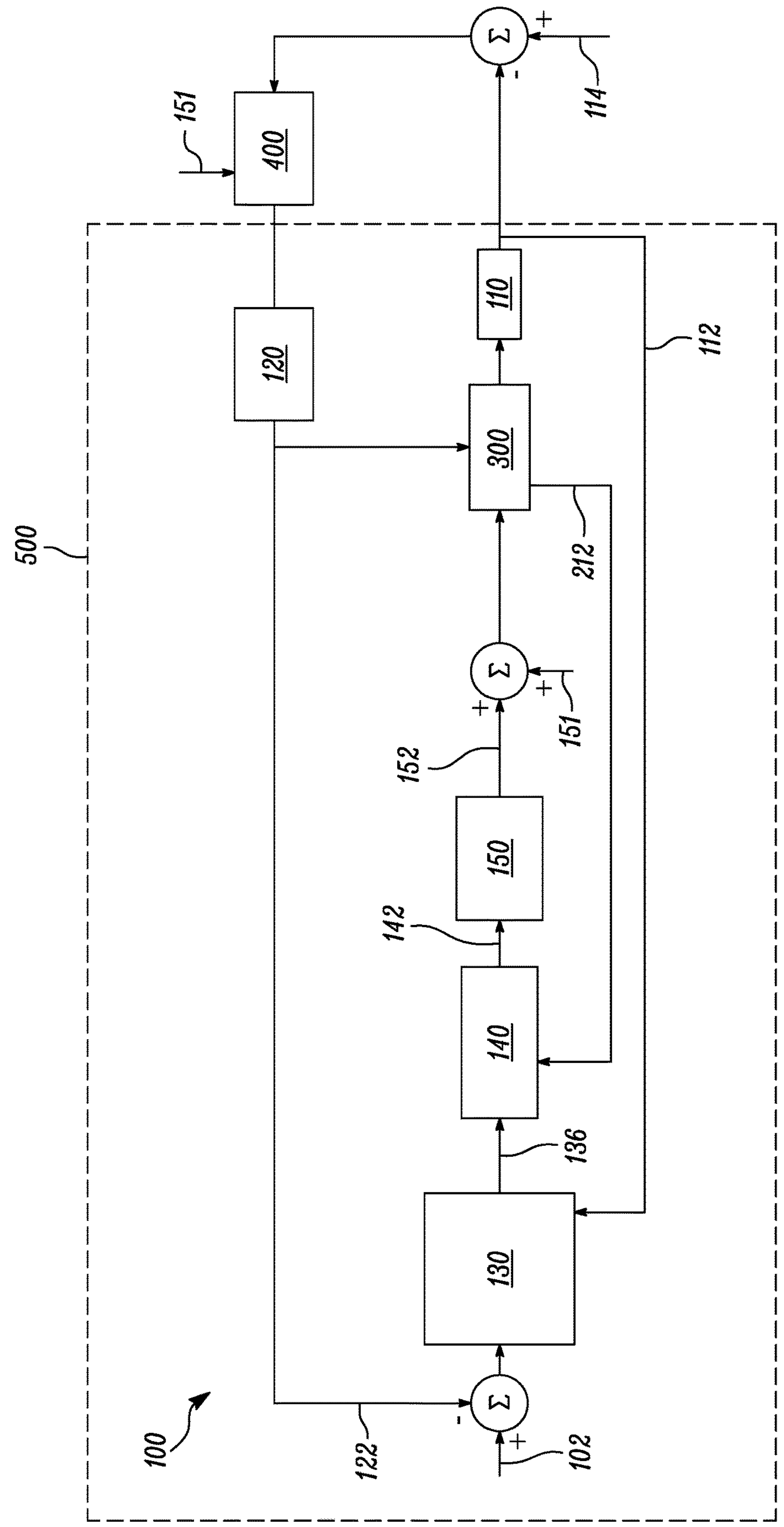
FIG. 2 is a schematic block diagram of a valve system including a valve and a system for controlling the valve, according to an embodiment of the present disclosure.

FIG. 2 illustrates a schematic block diagram of valve system 500 for use with fluid circuit 400 according to an embodiment of the present disclosure. As discussed above, valve system 500 includes valve 300, flow sensor 110, pressure sensor 120, adaptive controller 130, position controller 140, and valve actuator 150. In some embodiments, valve system 500 includes a system 100 for controlling valve 300 disposed in fluid communication with fluid circuit 400. System 100 includes flow sensor 110, pressure sensor 120, adaptive controller 130, position controller 140, and valve actuator 150.

Adaptive controller 130, position controller 140, and valve actuator 150 may reject external disturbing forces 151 which may allow system 100 to respond better to signal 102 indicative of the target pressure. External disturbing forces 151 may include mechanical forces, such as gravity bias of valve 300, and/or actuator shaft/bearing friction of valve 300. External disturbing forces 151 may also include patient induced forces, such as pressure forces (e.g., cough). A cough may release a large volume into patient circuit 604 in a very short time (~300 msec or less). This may create a rapid spike in the measured pressure. Valve 300 may ideally need to instantaneously correct pressure by relieving flow but also recover the PEEP immediately.

As discussed above, the actuating electric parameter essentially determines the fluid flow. This may facilitate precise and accurate tracking of the target pressure while reducing sensitivity to external disturbing forces 151. Accurate tracking of the target pressure may be essential for reducing patient expiratory effort, providing responsive trigger, and preventing lung collapse of patient 602 (shown in FIG. 1).

Since adaptive controller 130, position controller 140, and valve actuator 150 may reject external disturbing forces 151, other issues related to external disturbing forces 151 may also be resolved. These issues may include overshoot, slow convergence, valve fluttering, valve chattering, and oscillatory perturbations.

In some embodiments, valve system 500 may also receive a signal 114 indicative of a bias flow. The bias flow may be provided by other valves (not shown in FIG. 2) of ventilator 600 (shown in FIG. 1). The bias flow may cause the measured pressure to change. Therefore, the measured flow may be updated accordingly.

Figure 3:
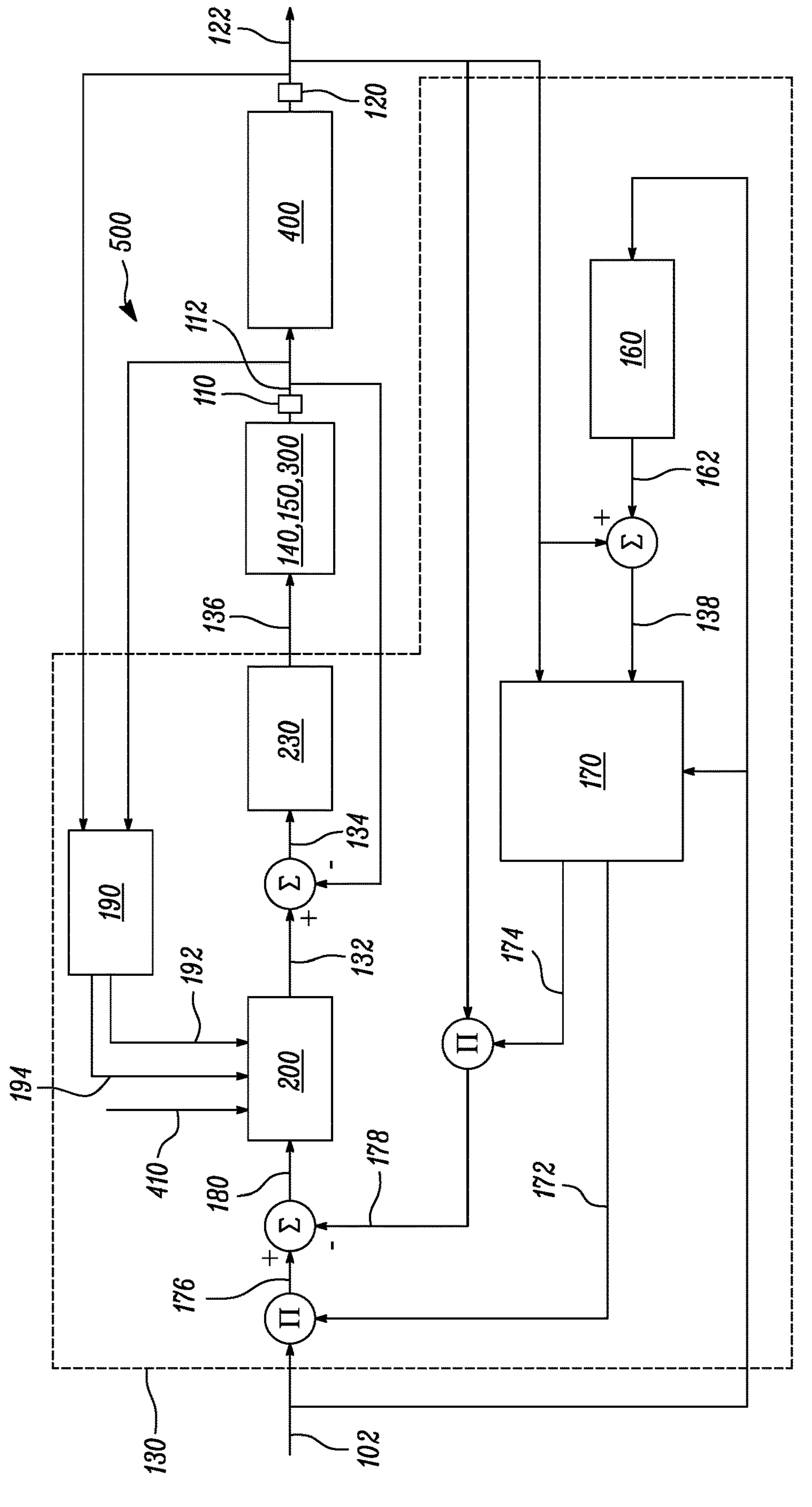
FIG. 3 is a detailed schematic block diagram of an adaptive controller of the valve system, according to an embodiment of the present disclosure.

FIG. 3 illustrates a detailed schematic block diagram of adaptive controller 130 of valve system 500 according to an embodiment of the present disclosure.

As discussed above, adaptive controller 130 is configured to receive signals 102, 112, 122 indicative of the target pressure, the measured flow, and the measured pressure, respectively.

Adaptive controller 130 is further configured to determine a desired flow based at least on the measured pressure, the measured flow, and the target pressure. In some embodiments, adaptive controller 130 is configured to generate a signal 132 indicative of the desired flow. In other words, adaptive controller 130 is configured to generate signal 132 indicative of the desired flow based at least on signals 102, 112, 122 indicative of the target pressure, the measured flow, and the measured pressure, respectively.

Adaptive controller 130 is further configured to determine a flow error 134 as a difference between the desired flow and the measured flow. Specifically, adaptive controller 130 is further configured to determine flow error 134 as a difference between the desired flow and the measured flow based on signals 132 and 112, respectively.

As discussed above, adaptive controller 130 is configured to determine the desired position of valve 300 and generate signal 136 indicative of the desired position of valve 300. Specifically, adaptive controller 130 is configured to determine the desired position of valve 300 based on flow error 134, such that flow error 134 is reduced. In the illustrated embodiment of FIG. 3, adaptive controller 130 is configured to determine, via a flow controller 230, the desired position of valve 300. In some embodiments, flow controller 230 may be a proportional integral derivative (PID) controller. This loop may assure that the measured flow follows the desired flow. Flow controller 230 may additionally provide anti-windup control with saturation limits matching physical limits of valve 300 between closed to open positions.

In some embodiments, adaptive controller 130 is further configured to determine, via a reference model 160, a model pressure based on the target pressure. In some embodiments, reference model 160 is configured to generate a signal 162 indicative of the model pressure based on the target pressure. In other words, reference model 160 is configured to generate signal 162 indicative of the model pressure based on signal 102 indicative of the target pressure. In some embodiments, a response of reference model 160 is obtained by solving Equation 1 provided below.

$$\frac{dy_m}{dt} = -a_m y_m + b_m u_c \tag{1}$$

where, $y_m$ is the model pressure, $u_c$ is the target pressure, and $a_m$ and $b_m$ are unknown positive constants.

Therefore, the response of reference model 160 is a function of the target pressure.

In some embodiments, adaptive controller 130 is further configured to determine a pressure error 138 as a difference between the measured pressure and the model pressure. Specifically, in some embodiments, adaptive controller 130 is further configured to determine pressure error 138 as a difference between the measured pressure and the model pressure based on signals 122, 162, respectively. Therefore, pressure error 138 is according to Equation 2 provided below:

$$e=y-y_m \tag{2}$$

where, e is pressure error 138, and y is the measured pressure.

In some embodiments, adaptive controller 130 is further configured to determine, via an adaptive control model 170, a first gain 172 and a second gain 174 based on the target pressure, the measured pressure, and pressure error 138. Specifically, in some embodiments, adaptive controller 130 is further configured to determine, via adaptive control model 170, first gain 172 and second gain 174 based on signal 102 indicative of the target pressure, signal 122 indicative of the measured pressure, and pressure error 138.

In some embodiments, adaptive controller 130 is further configured to determine a first product 176 as a product of first gain 172 and the target pressure. Specifically, adaptive controller 130 is further configured to determine first product 176 as the product of first gain 172 and signal 102 indicative of the target pressure.

In some embodiments, adaptive controller 130 is further configured to determine a second product 178 as a product of second gain 174 and the measured pressure. Specifically, adaptive controller 130 is further configured to determine second product 178 as the product of second gain 174 and signal 122 indicative of the measured pressure.

In some embodiments, adaptive controller 130 is further configured to determine an adaptive error 180 as a difference between first product 176 and second product 178.

Therefore, adaptive error 180 is according to Equation 3 provided below:

$$u=\theta_1 u_c-\theta_2 y \tag{3}$$

where, u is adaptive error 180, $\theta_1$ first gain 172, and $\theta_2$ is second gain 174.

Equation 4 below provides a process model.

$$\frac{dy}{dt}=-ay+bu \tag{4}$$

where, a and b are unknown positive constants.

Using Equations 1 to 4, Equation 5 is obtained and provided below.

$$\frac{de}{dt}=-a_m e-(b\theta_2+a-a_m)y+(b\theta_1-b_m)u_c \tag{5}$$

In some embodiments, adaptive control model 170 is based on the Lyapunov function that may assure control will be stable. Such adaptive control is known in the literature as direct model reference adaptive control.

In some embodiments, a candidate for Lyapunov function V is according to Equation 6 provided below. V is strictly positive real (i.e., V>0)

$$V(e,\theta_1,\theta_2)=\frac{1}{2}\left(e^2+\frac{1}{b\gamma}(b\theta_2+a-a_m)^2+\frac{1}{b\gamma}(b\theta_1-b_m)^2\right) \tag{6}$$

In some embodiments, a derivative of the candidate for Lyapunov function is according to Equation 7 provided below.

$$\frac{dV}{dt}=e\frac{de}{dt}+\frac{1}{\gamma}(b\theta_2+a-a_m)\frac{d\theta_2}{dt}+\frac{1}{\gamma}(b\theta_1-b_m)\frac{d\theta_1}{dt} \tag{7}$$

Solving Equation 7 further gives Equation 8 and is provided below.

$$\frac{dV}{dt}=-a_m e^2+\frac{1}{\gamma}(b\theta_2+a-a_m)\left(\frac{d\theta_2}{dt}-\gamma ye\right)+\frac{1}{\gamma}(b\theta_1-b_m)\left(\frac{d\theta_1}{dt}+\gamma u_c e\right) \tag{8}$$

Using adaptation law, Equations 9 and 10 are determined and provided below.

$$\frac{d\theta_1}{dt}=-\gamma u_c e \tag{9}$$

$$\frac{d\theta_2}{dt}=\gamma yee \tag{10}$$

Equations 9 and 10 are integrated to determine $\theta_1$ and $\theta_2$.

Using Equations 8 to 10, Equation 11 is obtained and is provided below.

$$\frac{dV}{dt}=-a_m e^2 \tag{11}$$

Equation 11 is integrated to obtain Equation 12 provided below.

$$V=-2a_m e\frac{de}{dt} \tag{12}$$

Using Equations 12 and 5, Equation 13 is obtained and provided below $$V=2a_m e(-a_m e-(b\theta_2+a-a_m)y+(b\theta_1-b_m)u_c) \tag{13}$$

Reference model 160 is used to determine an expected response of valve system 500 (i.e., the model pressure) from an actual response of valve system 500 (i.e., the measured pressure). The adaptive law determines first gain 172 and second gain 174, such that a difference between the expected response and the actual response is reduced.

Reference model 160 and adaptive control model 170 may dynamically force pressure control loop response to follow the response of reference model 160.

Thus, valve system 500 may automatically determine required instantaneous gain adjustments without a need for prior valve profile information (e.g., calibration). This may further provide faster and more accurate tracking of the target pressure, such as the pressure trajectory signal.

In some embodiments, adaptive controller 130 is further configured to determine, via a dynamic estimator 190, an estimated resistance and an estimated compliance based on the measured pressure and the measured flow. The estimated resistance and the estimated compliance are real-time estimates. Therefore, dynamic estimator 190 may consider the dynamic loads, such as different patients from neonatal to adult and all their possible pathologies.

In some embodiments, adaptive controller 130 is configured to generate, via dynamic estimator 190, a signal 192 indicative of the estimated resistance and a signal 194 indicative of the estimated compliance based on the measured pressure and the measured flow. In other words, adaptive controller 130 is configured to generate, via dynamic estimator 190, signal 192 indicative of the estimated resistance and signal 194 indicative of the estimated compliance based on signal 122 indicative of the measured pressure and signal 112 indicative of the measured flow. In some embodiments, each of the estimated resistance and the estimated compliance corresponds to an object (not shown) disposed in fluid communication with fluid circuit 400. In some embodiments, the object may be patient 602 (shown in FIG. 1). Specifically, the object may be lungs (not shown) of patient 602. In such embodiments, the estimated resistance may be an estimated lung airway resistance. Similarly, the estimated compliance may be the estimated lung compliance.

In some embodiments, adaptive controller 130 is further configured to receive a signal 410 indicative of a tubing compliance of fluid circuit 400 and determine, via an adaptive lag compensator 200, the desired flow based on the estimated resistance, the estimated compliance, the tubing compliance, and adaptive error 180. The tubing compliance may be a measured compliance and/or a calibrated compliance of fluid circuit 400.

In some embodiments, adaptive controller 130 is configured to generate, via adaptive lag compensator 200, signal 132 indicative of the desired flow based on the estimated resistance, the estimated compliance, the tubing compliance, and adaptive error 180. In other words, adaptive controller 130 is configured to generate, via adaptive lag compensator 200, signal 132 indicative of the desired flow based on based signal 192 indicative of the estimated resistance, signal 194 indicative of the estimated compliance, signal 410 indicative of the tubing compliance, and adaptive error 180.

In some embodiments, a response of dynamic estimator 190 is according to Equation 14 provided below:

$$\frac{P_{exh}(s)}{Q_{exh}(s)} = \frac{s + \frac{1}{\hat{R}_L \hat{C}_L}}{sC_T\left(s + \frac{\hat{C}_L + C_T}{\hat{R}_L \hat{C}_L C_T}\right)} \tag{14}$$

where, $P_{exh}$ is the measured pressure, $Q_{exh}$ is the measured flow, $\hat{R}_L$ is the estimated resistance, $\hat{C}_L$ is the estimated compliance, and $C_T$ is the tubing compliance.

In some embodiments, a response of adaptive lag compensator 200 is according to Equation 15 provided below:

$$\frac{Q_{traj}(s)}{E_P(s)} = \frac{C_T\left(s + \frac{\hat{C}_L + C_T}{\hat{R}_L \hat{C}_L C_T}\right)}{s + \frac{1}{\hat{R}_L \hat{C}_L}} \tag{15}$$

where, $Q_{traj}$ is the desired flow, and $E_p$ is adaptive error 180.

In the above Equations 14 and 15, 's' is a LaPlace operator modeling a linear, continuous time, and physical system. s=σ+jω), where ω is a frequency of the complex plane and σ is a real component.

Equation 15 in discrete form is provided below as Equation 16.

$$Q_{traj}(n) = \beta E_P(n) - \gamma E_P(n-1) + \alpha E_P(n-1) \tag{16}$$

where, $$\beta = \frac{(\hat{C}_L + C_T)\Delta T + \hat{R}_L \hat{C}_L C_T}{\hat{R}_L \hat{C}_L + \Delta T}$$

$$\gamma = \frac{\hat{R}_L \hat{C}_L C_T}{\hat{R}_L \hat{C}_L + \Delta T}$$

$$\alpha = \frac{\hat{R}_L \hat{C}_L}{\hat{R}_L \hat{C}_L + \Delta T}$$

where,

ΔT is an update interval.

Adaptive lag compensator 200 may essentially cancel the zero and non-integrator pole of fluid circuit 400. Valve actuator 150 may control the valve flow area and adaptive controller 130 may track the target pressure.

Figure 4:
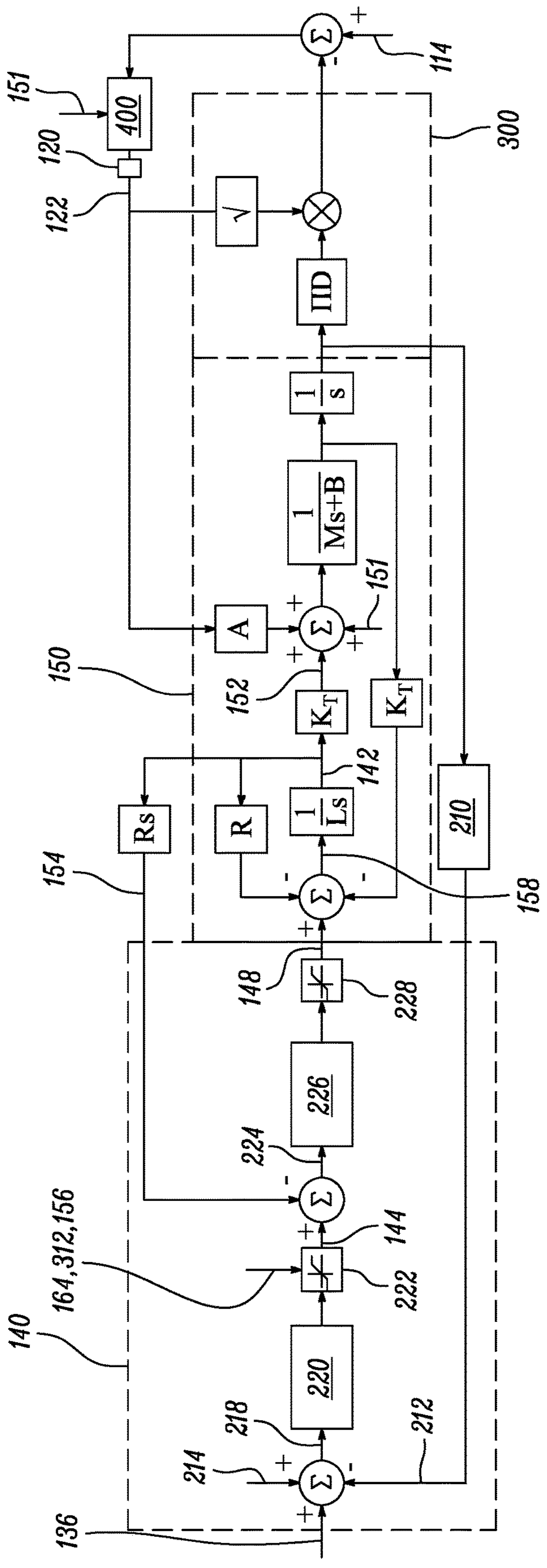
FIG. 4 is a detailed schematic block diagram of a position controller, a valve actuator, and the valve, according to an embodiment of the present disclosure.

FIG. 4 is a detailed schematic block diagram of position controller 140, valve actuator 150, and valve 300 according to an embodiment of the present disclosure.

In some embodiments, valve system 500 (shown in FIG. 3) further includes a position sensor 210. In some other embodiments, system 100 (shown in FIG. 3) includes position sensor 210. In some other embodiments, valve 300 includes position sensor 210. Position sensor 210 is communicably coupled to position controller 140 and configured to determine a measured position of valve 300. In some embodiments, position sensor 210 is configured to generate a signal 212 indicative of the measured position of valve 300 determined by position sensor 210. In some embodiments, position sensor 210 includes a linear optical encoder.

In some embodiments, position controller 140 is further configured to receive a signal 214 indicative of a bias position of valve 300. The bias position shifts a zero position (i.e., the closed position) past a valve seat 310 (shown in FIG. 5) associated with valve 300 to prevent leaks.

In some embodiments, position controller 140 is further configured to determine a position sum as a sum of the desired position and the bias position. In other words, position controller 140 is configured to determine the position sum as the sum of the desired position based on signal 136 and the bias position based on signal 214. Position controller 140 may receive signal 136 from flow controller 230 (shown in FIG. 3).

In some embodiments, position controller 140 is further configured to determine a position error 218 as a difference between the position sum and the measured position. In some embodiments, position controller 140 is further configured to determine a desired electric parameter by applying a first lead-lag compensator 220 and a first limiter 222 on position error 218. In some embodiments, position controller 140 is configured to generate a signal 144 indicative of the desired electric parameter by applying first lead-lag compensator 220 and first limiter 222 on position error 218. In some embodiments, first limiter 222 is configured to limit the desired electric parameter within a first maximum limit. In some embodiments, the first maximum limit is a physical amplifier limit.

In some embodiments, position controller 140 is further configured to receive a feedback signal 154 from valve actuator 150. Feedback signal 154 is indicative of the actuating electric parameter. In some cases, feedback signal 154 is a voltage that is proportional to the actuating electric parameter by a resistor value Rs.

In some embodiments, position controller 140 is further configured to determine a controlling parameter error 224 as a difference between the desired electric parameter and feedback signal 154. In other words, position controller 140 is configured to determine controlling parameter error 224 as the difference between the desired electric parameter based on signal 144 and feedback signal 154.

In some embodiments, position controller 140 is further configured to determine a controlling electric parameter by applying a second lead-lag compensator 226 and a second limiter 228 on controlling parameter error 224. In some embodiments, position controller 140 is configured to generate a signal 148 indicative of the controlling electric parameter by applying second lead-lag compensator 226 and second limiter 228 on controlling parameter error 224. In some embodiments, second limiter 228 is configured to limit the controlling electric parameter within a second maximum limit. In some embodiments, the second maximum limit is within a range of an analog power amplifier (not shown) that connects position controller 140 to valve actuator 150.

In some embodiments, position controller 140 is further configured to receive signals 164, 312, 156 indicative of a desired maximum pressure, an effective cross-sectional area of valve seat 310 (shown in FIG. 5) associated with valve 300, and a force constant of valve actuator 150, respectively. In some embodiments, position controller 140 is further configured to determine the first maximum limit based on the desired maximum pressure, the effective cross-sectional area, and the force constant. In other words, position controller 140 is configured to determine the first maximum limit based on signals 164, 312, 156 indicative of the desired maximum pressure, the effective cross-sectional area, and the force constant, respectively. Specifically, the desired maximum pressure, the effective cross-sectional area, and the force constant may be provided to first limiter 222. Thus, the first maximum limit may be adjustable and dynamically updated. This may help to overcome lag.

In some embodiments, the desired maximum pressure, the effective cross-sectional area, and the force constant may be provided to first limiter 222 according to Equation 17 provided below.

$$i_{max} = \frac{PA}{K_T} \tag{17}$$

where, $i_{max}$ is the first maximum limit,

P is the desired maximum pressure,

A is the effective cross-sectional area, and $K_T$ is the force constant.

In some embodiments, position controller 140 is a digital signal processor (DSP). In some embodiments, position controller 140 executes processing cycles at a 100 kHz clock rate.

In some embodiments, valve actuator 150 is configured to determine an actuating parameter error 158 based at least on a difference between the controlling electric parameter determined by position controller 140 and the actuating electric parameter. In other words, valve actuator 150 is configured to determine actuating parameter error 158 based at least on the difference between the controlling electric parameter based on signal 148 and the actuating electric parameter based on signal 142. In some embodiments, valve actuator 150 is further configured to apply actuating force 152 on valve 300 based on actuating parameter error 158.

In the illustrated example, valve actuator 150 is a linear voice coil actuator including a moving coil of mass M suspended strictly by a bearing with viscous friction B. Actuating force 152 is generated by the action of the actuating electric parameter to the coil with a coil resistance R and an inductance L.

Actuating force 152 is proportional to the actuating electric parameter, but actuating parameter error 158 may be diminished according to instantaneous velocity of the coil. Further, actuating force 152 may be challenged by external disturbing forces 151. The measured pressure may rise from external disturbing forces 151 by a factor of A, i.e., a contact cross-sectional area of valve 300. Thus, the factor of A may apply only when valve 300 is fully closed or nearly closed. The factor of A may be diminished as valve 300 opens and flow proceeds. Therefore, valve actuator 150 is a dynamic valve actuator.

Second lead-lag compensator 226 of position controller 140 may provide faster electric parameter injection by cancelling actuator electrical pole R/L, and replacing it with a faster dynamic. Position controller 140 may further overcome disturbance of reverse electromotive force (EMF) that may manifest from motion of valve actuator 150.

As discussed above, actuating force 152 is applied on valve 300 based at least on the actuating electric parameter in order to control the fluid flow. In case of a linear, cylindrical valve, the desired position of valve 300 may determine a cylindrical flow area $\pi D$, where D is a diameter of valve 300. In some embodiments, a product of the cylindrical flow area $\pi D$ and a square root of the measured pressure may provide the fluid flow. Thus, the desired position modulates the measured pressure to provide the fluid flow.

Unlike conventional control of valves where the controlled variable is force, the controlled variable of valve 300 is flow. This is accomplished by getting valve 300 to follow the desired position, which may effectively control the valve flow area (e.g., cylindrical flow area $\pi D$) of valve 300. Thus, system 100 and valve system 500 shown in FIG. 1 may enable accurate tracking of the target pressure by controlling flow rather than force. Controlling flow may be comparatively easier as actuating force 152 may be significantly greater than external disturbing forces 151. Further, adaptive controller 130, position controller 140, and valve actuator 150 may reject external disturbing forces 151 which may allow system 100 to respond better to signal 102 indicative of the target pressure.

Flow control may further provide a good control of pressure when valve 300 is nearly closed, but it may also enable a way to control pressure during the start of exhalation and the transition from end inhalation pressure to the target pressure when valve 300 is open and may allow the bulk flow of the exhaled gas to occur.

Figure 5:
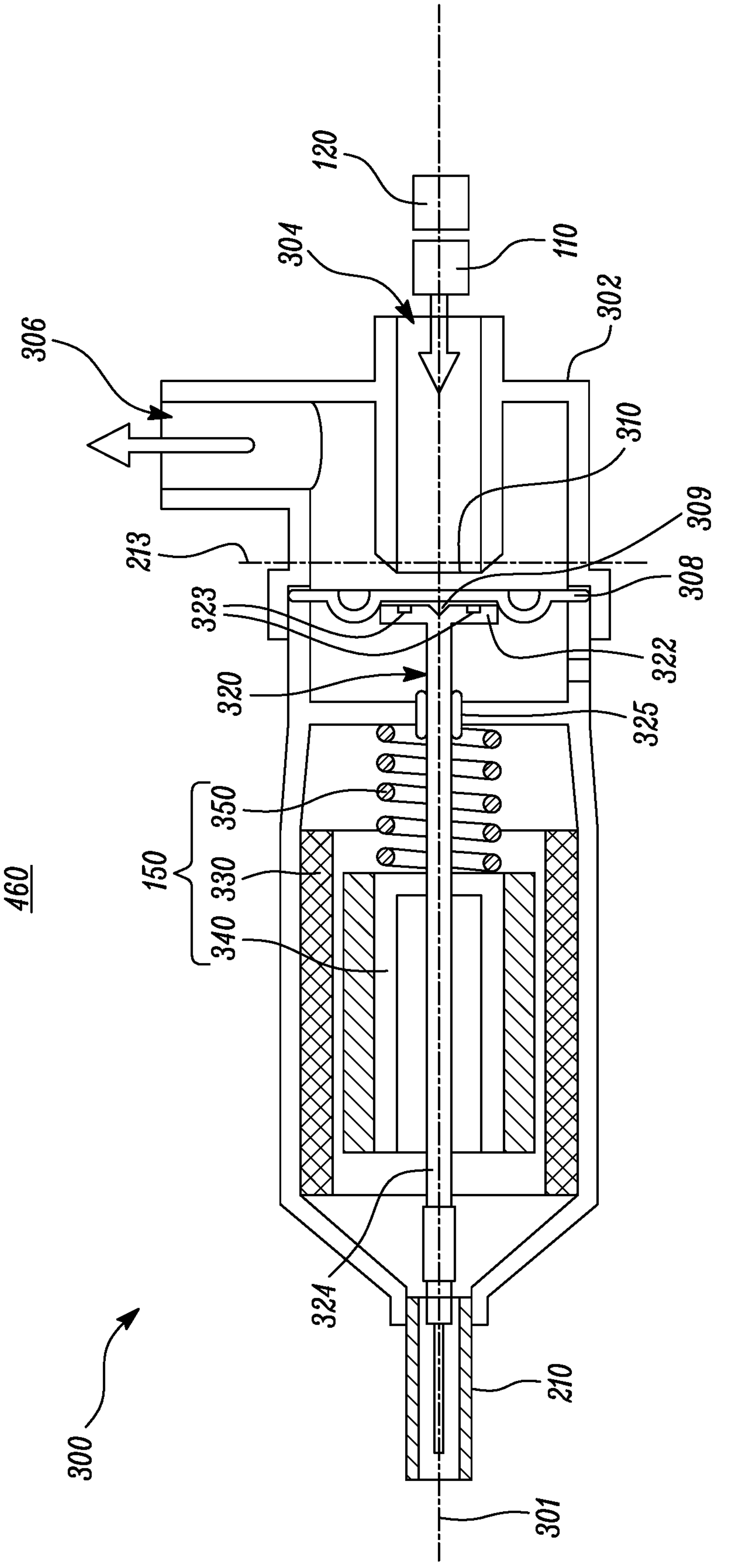
FIG. 5 is a schematic sectional side view of the valve, according to a first embodiment of the present disclosure.

FIG. 5 illustrates a schematic sectional side view of valve 300 according to a first embodiment of the present disclosure.

As discussed above, valve 300 includes valve housing 302 defining inlet port 304 disposed in fluid communication with fluid circuit 400 (shown in FIG. 1) and exhaust port 306 disposed in fluid communication with environment 460 external to valve 300.

Valve 300 further includes a valve body 320 at least partially received within valve housing 302 and movable relative to valve housing 302. Valve body 320 is configured to control the fluid flow between inlet port 304 and exhaust port 306. In the illustrated embodiment of FIG. 5, valve 300 further includes position sensor 210.

As discussed above, position controller 140 (shown in FIG. 4) is configured to determine the actuating electric parameter based at least on the desired position of valve 300. Specifically, position controller 140 is configured to determine the actuating electric parameter based at least on the desired position of valve body 320.

Further, as discussed above, valve actuator 150 (shown in FIG. 4) is configured to apply actuating force 152 on valve 300 based at least on the actuating electric parameter. Specifically, valve actuator 150 is configured to apply actuating force 152 on valve body 320 based at least on the actuating electric parameter in order to control the fluid flow from inlet port 304 to exhaust port 306.

Position sensor 210 is configured to determine the measured position of valve 300. Specifically, position sensor 210 is configured to determine the measured position of valve body 320 relative to valve housing 302. Further, position controller 140 is further configured to receive signal 214 (shown in FIG. 4) indicative of the bias position of valve body 320.

In the illustrated embodiment of FIG. 5, valve 300 further includes valve seat 310 disposed adjacent to inlet port 304 and a membrane 308 coupled to valve housing 302. Membrane 308 is configured to selectively engage with valve seat 310 to close inlet port 304.

Valve body 320 includes a disc 322 coupled to membrane 308 and a stem 324 extending from disc 322 along a longitudinal axis 301. Valve body 320 is configured to move membrane 308 along longitudinal axis 301 based on actuating force 152 applied by valve actuator 150 on stem 324.

In some embodiments, disc 322 may be embedded with high strength magnets 323. Magnets 3232 may attract a ferromagnetic backing 309. In some embodiments, backing 309 may be bonded to membrane 308 opposite to disc 322. Backing 309 and disc 322 may be configured such that when magnetic forces attract disc 322 and membrane 308, disc 322 self-centers onto membrane 308.

In the illustrated embodiment of FIG. 5, valve actuator 150 is a linear actuator. Valve actuator 150 includes a stator 330 including a permanent magnet. Valve actuator 150 further includes a coil 340 coupled to stem 324 of valve body 320. Coil 340 is configured to apply actuating force 152 on stem 324 based on the actuating electric parameter in order to move stem 324 along longitudinal axis 301. Movement of stem 324 may be constrained along longitudinal axis 301 (i.e., rectilinear motion) by a rear suspension (not shown), such as bearing, bushing, or flexure and a front suspension (not shown) and a dust seal 325.

Valve actuator 150 further includes a spring 350 engaged with valve body 320 and configured to bias valve body 320 away from valve seat 310. This may allow patient 602 (shown in FIG. 1) to exhale gas upon loss of power. Specifically, valve 300 will open via spring 350 upon loss of power to permit the exhaled gas to flow to environment 460 through valve 300.

Coil 340 is rigidly attached to stem 324 so that actuating force 152 may be coupled into moving stem 324 in either direction depending on the actuating electric parameter. Thus, valve 300 provides symmetric push-pull capability to properly track the desired flow. Since coil 340 is rigidly attached to stem 324, coil 340 of valve actuator 150 may never separate from valve body 320 of valve 300 during operation. Coil 340 of valve actuator 150 and valve body 320 of valve 300 may only be separated when intentionally separated for cleaning or replacement purposes.

Further, a zero position 213 of valve 300 is shown. As discussed above, the bias position may shift zero position 213 past valve seat 310 to prevent leaks. Zero position 213 may be designed by either adjusting a position of position sensor 210 further towards right or by increasing a value of the bias position.

Figure 6:
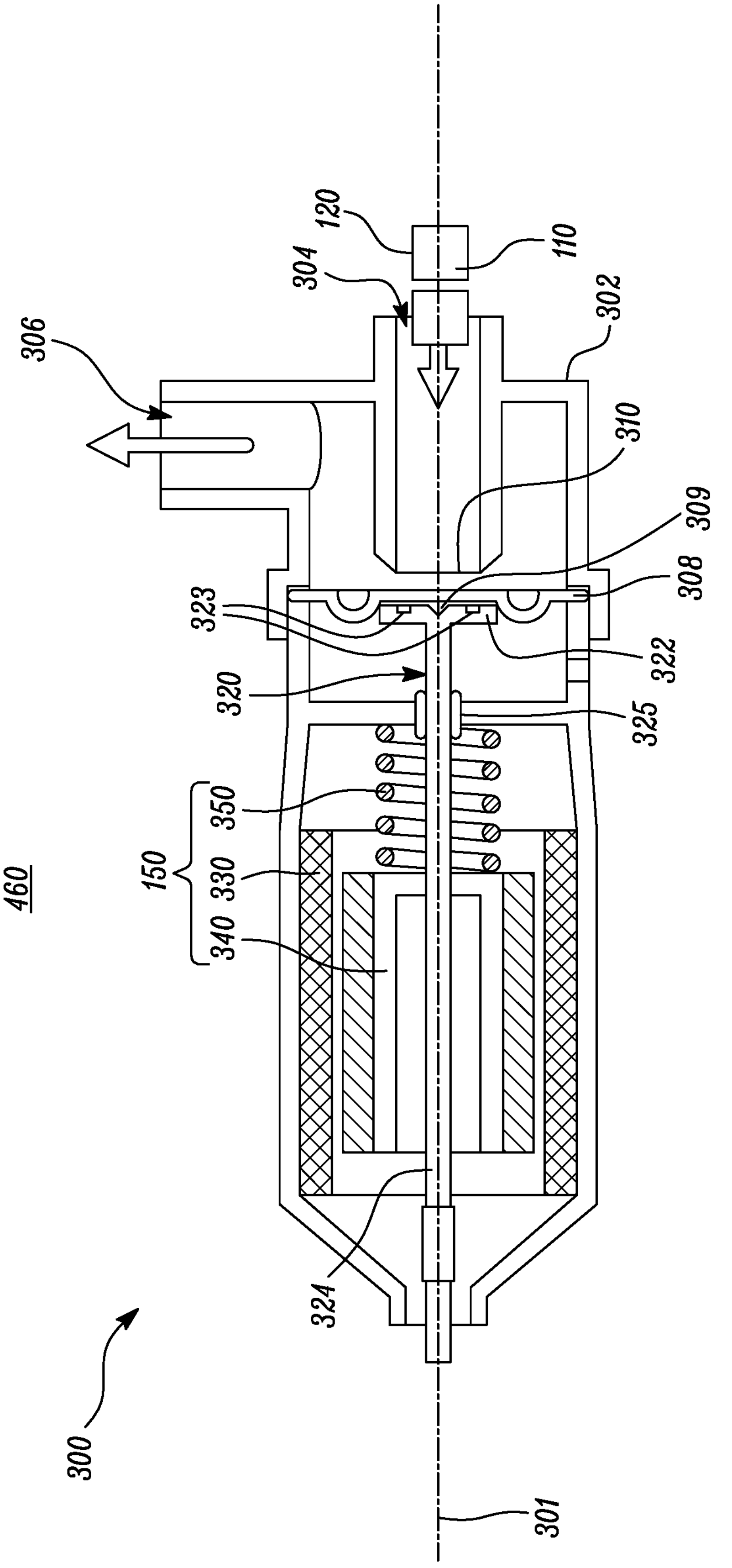
FIG. 6 is a schematic sectional side view of the valve, according to a second embodiment of the present disclosure.

FIG. 6 illustrates a schematic sectional side view of valve 300 according to a second embodiment of the present disclosure. Valve 300 is substantially similar to valve 300 of FIG. 5. However, valve 300 of FIG. 6, does not include position sensor 210. In this embodiment, desired position may be controlled by balancing actuating force 152 against a stiff spring (for example, a stiffer configuration of spring 350), such that actuating force 152 is much greater than external disturbing forces 151 (shown in FIG. 2), that may include the gravity bias of valve 300, and/or the actuator shaft/bearing friction of valve 300.

Figure 7B:
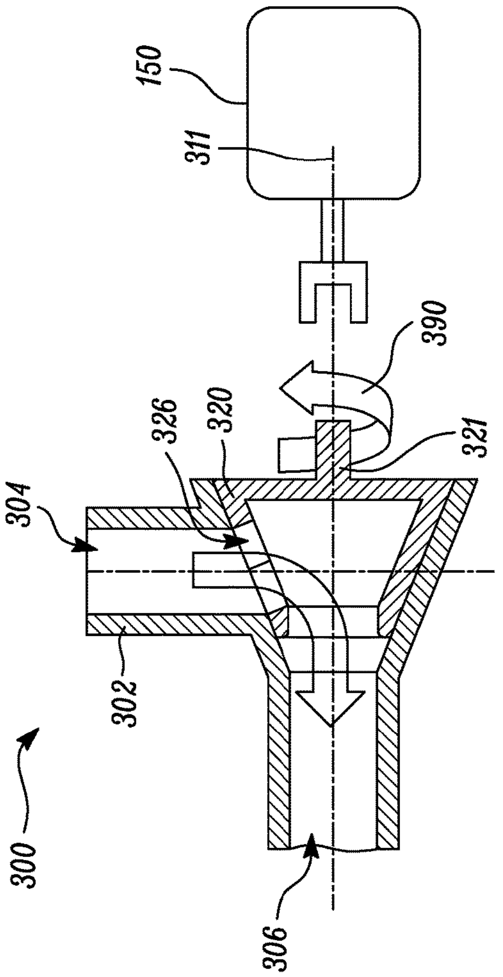
FIG. 7B is a schematic sectional side view of the valve, according to the third embodiment of the present disclosure.
Figure 7C:
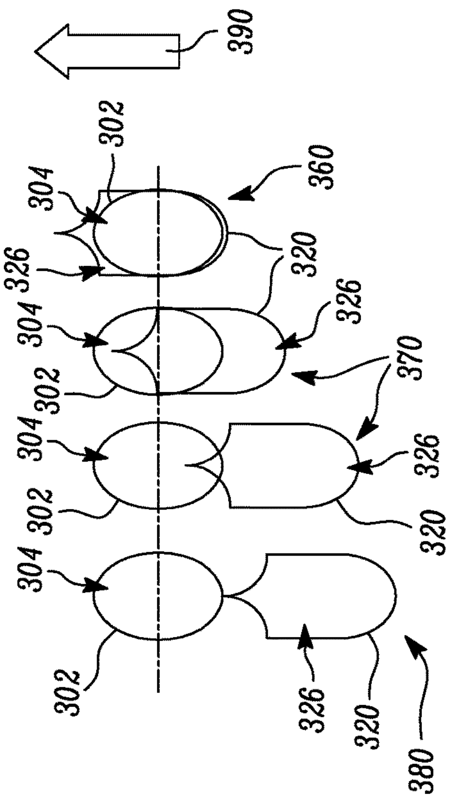
FIG. 7C is a schematic view of a valve body and a valve housing of the valve in different positions relative to each other, according to the third embodiment of the present disclosure; and, FIG. 8 is a flowchart depicting a method for controlling the valve disposed in fluid communication with the fluid circuit, according to an embodiment of the present disclosure.
Figure 7A:
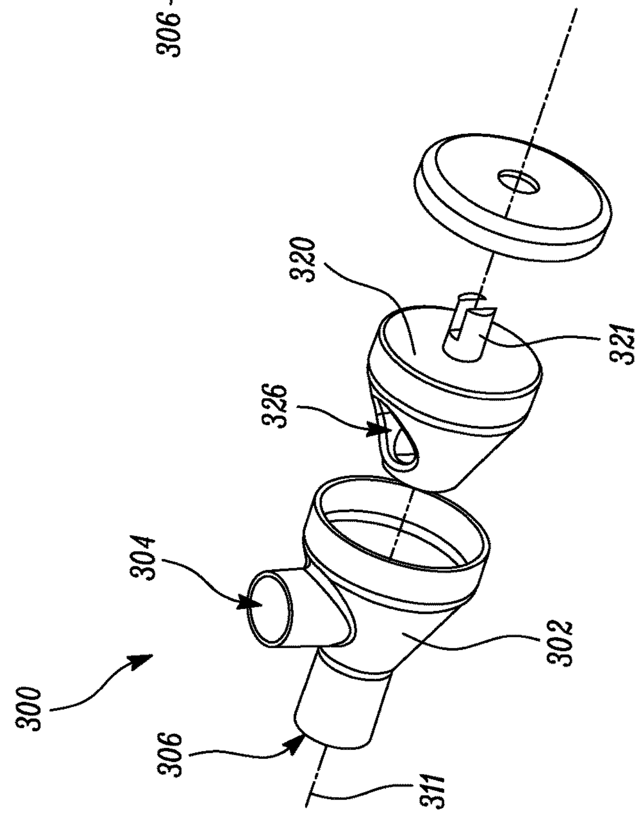
FIG. 7A is a schematic exploded perspective view of the valve, according to a third embodiment of the present disclosure.

FIG. 7A illustrates a schematic exploded perspective view of valve 300 according to a third embodiment of the present disclosure. FIG. 7B illustrates a schematic sectional side view of valve 300 according to the third embodiment of the present disclosure. FIG. 7C illustrates a schematic view of valve body 320 and valve housing 302 of valve 300 in an open position 360, metering positions 370, and a closed position 380 according to the third embodiment of the present disclosure.

As discussed above, valve 300 includes valve housing 302 defining inlet port 304 disposed in fluid communication with fluid circuit 400 (shown in FIG. 1) and exhaust port 306 disposed in fluid communication with environment 460 external to valve 300. Valve 300 further includes valve body 320 at least partially received within valve housing 302 and movable relative to valve housing 302. In some embodiments, valve body 320 may at least be partially received and fit tightly within valve housing 302. Hence, valve housing 302 may never separate from valve body 320 which is coupled to valve actuator 150 during operation. Valve housing 302 and valve body 320 may only be separated when intentionally separated for cleaning or replacement purposes.

In the illustrated embodiment of FIGS. 7A-7C, valve body 320 is rotatable relative to valve housing 302 about a rotational axis 311. Further, valve body 320 defines a body port 326 therethrough. A rotation of valve body 320 relative to valve housing 302 controls a degree of overlap between body port 326 and at least one of inlet port 304 and exhaust port 306. Specifically, in the illustrated embodiment, the rotation of valve body 320 relative to valve housing 302 controls a degree of overlap between body port 326 and inlet port 304. In some embodiments, body port 326 may be tapered as illustrated in FIG. 7C. Body port 326 that is tapered may provide higher sensitivity of flow control near closed position 380.

Further, as discussed above, valve actuator 150 is configured to apply actuating force 152 on valve body 320 based at least on the actuating electric parameter in order to control fluid flow from inlet port 304 to exhaust port 306. In the illustrated embodiment of FIGS. 7A-7C, valve actuator 150 is configured to apply actuating force 152 on valve body 320 in order to rotate valve body 320 relative to valve housing 302. In some embodiments, valve actuator 150 may be a servo controlled motor that connects to valve body 320 via a mating shaft 321.

Further, actuating force 152 may couple into valve body 320 (e.g., by mating shaft 321) in either direction depending on the actuating electric parameter. Thus, valve 300 provides symmetric clockwise and anticlockwise rotation capability to properly track the desired flow. Valve body 320 of valve 300 is shown rotating in a rotational direction 390 relative to valve housing 302. In the illustrated embodiment of FIGS. 7B and 7C, rotational direction 390 is a clockwise direction.

In some embodiments, a torsional spring (not shown) on valve actuator 150 may freely rotate valve 300 to the open position 360 when power is lost. This may allow patient 602 (shown in FIG. 1) to exhale gas upon loss of power. Specifically, valve 300 will open via the torsional spring upon loss of power to permit the exhaled gas to flow to environment 460 (shown in FIG. 1) through valve 300.

Referring to FIGS. 5 to 7A-7C, in some embodiments, valve 300 may include re-useable, sterilizable plastic components. In some other embodiments, valve 300 be disposable or one or more components of valve 300 may be disposable. In some embodiments, moving parts (e.g., stem 324 or valve body 320) may include injection moldable plastics, such as acetal resins (POM), polybutylene teraphalate (PBT), or nylon polyamide (PA) that may be tough, abrasion resistant, having a very low coefficient of friction. Such injection moldable plastics may further have low water absorption and may be dimensionally stable.

Figure 8:
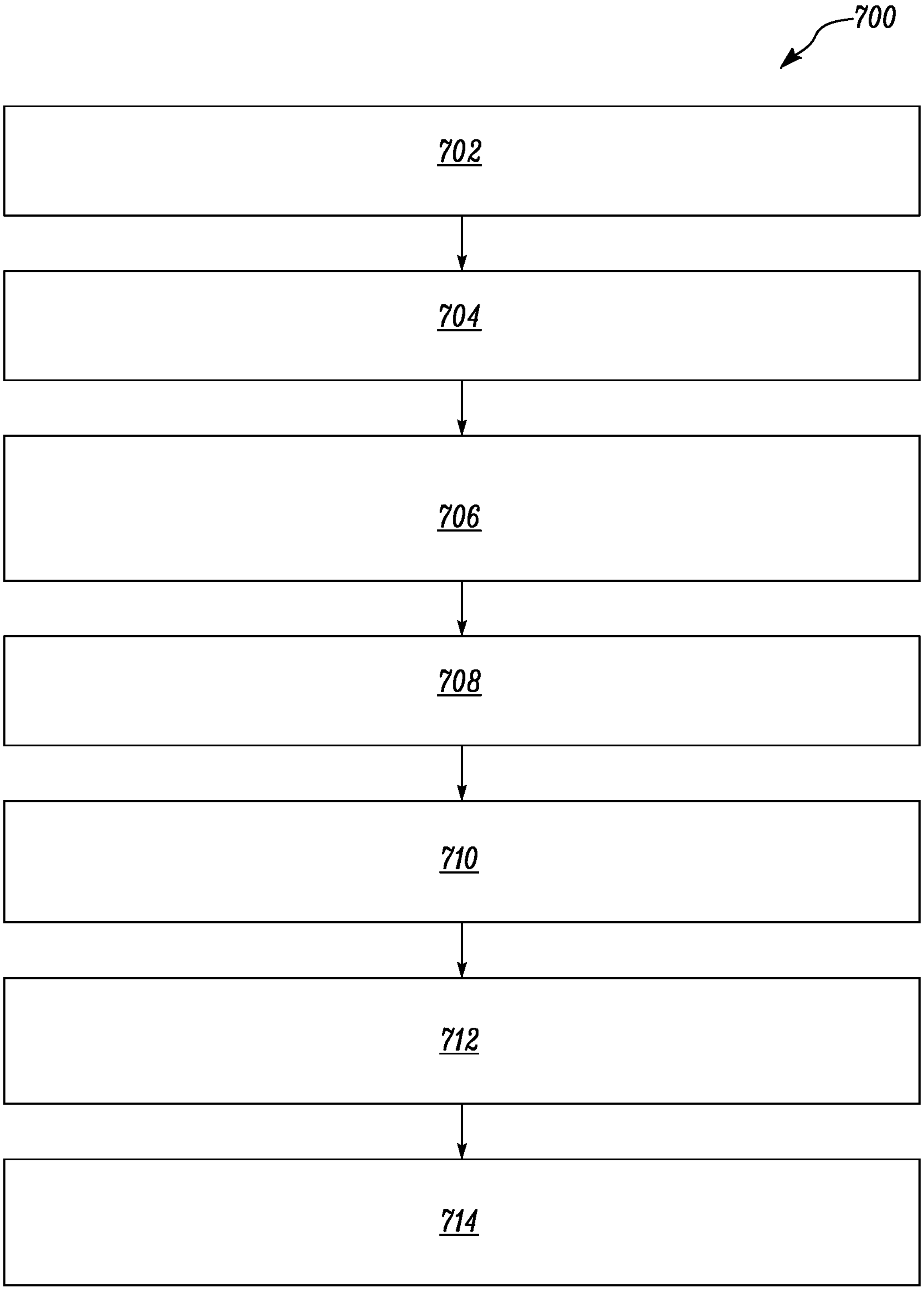

FIG. 8 illustrates a flowchart depicting a method 700 for controlling valve 300 (shown in FIG. 1) disposed in fluid communication with fluid circuit 400 (shown in FIG. 1) according to an embodiment of the present disclosure. Method 700 will be further described with reference to FIGS. 1 to 7.

At step 702, method 700 includes determining the measured flow of fluid flowing from fluid circuit 400 to valve 300.

At step 704, method 700 includes determining the measured pressure of fluid flowing from fluid circuit 400 to valve 300.

At step 706, method 700 includes determining the desired flow based at least on the measured pressure, the measured flow, and the target pressure.

In some embodiments, determining the desired flow further includes determining, via reference model 160, the model pressure based on the target pressure. In some embodiments, determining the desired flow further includes determining pressure error 138 as the difference between the measured pressure and the model pressure. In some embodiments, determining the desired flow further includes determining, via adaptive control model 170, first gain 172 and second gain 174 based on the target pressure, the measured pressure, and pressure error 138. In some embodiments, determining the desired flow further includes determining first product 176 as the product of first gain 172 and the target pressure. In some embodiments, determining the desired flow further includes determining second product 178 as the product of second gain 174 and the measured pressure. In some embodiments, determining the desired flow further includes determining adaptive error 180 as the difference between first product 176 and second product 178.

In some embodiments, determining the desired flow further includes determining, via dynamic estimator 190, the estimated resistance and the estimated compliance based on the measured pressure and the measured flow. Each of the estimated resistance and the estimated compliance corresponds to the object disposed in fluid communication with fluid circuit 400. In some embodiments, determining the desired flow further includes receiving signal 410 indicative of the tubing compliance of fluid circuit 400. In some embodiments, determining the desired flow further includes determining, via adaptive lag compensator 200, the desired flow based on the estimated resistance, the estimated compliance, the tubing compliance, and adaptive error 180.

At step 708, method 700 includes determining flow error 134 as the difference between the desired flow and the measured flow.

At step 710, method 700 includes determining the desired position of valve 300 based on flow error 134, such that flow error 134 is reduced.

At step 712, method 700 includes determining the actuating electric parameter based at least on the desired position of valve 300.

In some embodiments, determining the actuating electric parameter further includes determining the measured position of valve 300. In some embodiments, determining the actuating electric parameter further includes receiving signal 214 indicative of the bias position of valve 300.

In some embodiments, determining the actuating electric parameter further includes determining the position sum as the sum of the desired position and the bias position. In some embodiments, determining the actuating electric parameter further includes determining position error 218 as the difference between the position sum and the measured position.

In some embodiments, determining the actuating electric parameter further includes determining the desired electric parameter by applying first lead-lag compensator 220 and first limiter 222 on position error 218. First limiter 222 is configured to limit the desired electric parameter within the first maximum limit. In some embodiments, method 700 incudes receiving signals 164, 312, 156 indicative of the desired maximum pressure, the effective cross-sectional area of valve seat 310 associated with valve 300, and the force constant of valve actuator 150 configured to apply actuating force 152 on valve 300. In some embodiments, method 700 further incudes determining the first maximum limit based on the desired maximum pressure, the effective cross-sectional area, and the force constant.

In some embodiments, determining the actuating electric parameter further includes receiving feedback signal 154 indicative of the actuating electric parameter. In some embodiments, determining the actuating electric parameter further includes determining controlling parameter error 224 as the difference between the desired electric parameter and feedback signal 154. In some embodiments, determining the actuating electric parameter further includes determining the controlling electric parameter by applying second lead-lag compensator 226 and second limiter 228 on controlling parameter error 224. Second limiter 228 is configured to limit the controlling electric parameter within the second maximum limit.

At step 714, method 700 includes applying actuating force 152 on valve 300 based at least on the actuating electric parameter.

In some embodiments, applying actuating force 152 further includes determining actuating parameter error 158 based at least on the difference between the controlling electric parameter and the actuating electric parameter. In some embodiments, applying actuating force 152 further includes applying actuating force 152 on valve 300 based on the actuating parameter error.

Therefore, method 700, system 100, and valve system 500 may enable tracking of the target pressure precisely from start to end of exhalation, regardless of settings (e.g., PEEP or any other therapy settings of ventilator 600) or load (e.g., different patients). Accurate tracking of the target pressure may be essential for reducing the patient expiratory effort, providing responsive trigger, and preventing lung collapse of patient 602 (shown in FIG. 1).

Further, method 700, system 100, and valve system 500 may allow greater precision tracking of the target pressure without the need for prior valve profile information, such as the valve calibration or other prior profile information that may be required in conventional systems and methods for controlling a valve. Specifically, method 700, system 100, and valve system 500 may automatically determine required instantaneous gain adjustments without the need for the calibration or the other prior valve profile information.

Further, method 700, system 100, and valve system 500 may recognize the relation between pressure and flow is nonlinear and that the dynamics can vary significantly between different loads (e.g., different patients and pressures within the breath itself). Accordingly, method 700, system 100, and valve system 500 utilize nonlinear controls that may automatically and continuously adjust with the different loads.

Unless otherwise indicated, all numbers expressing feature sizes, amounts, and physical properties used in the specification and claims are to be understood as being modified by the term "about". Accordingly, unless indicated to the contrary, the numerical parameters set forth in the foregoing specification and attached claims are approximations that can vary depending upon the desired properties sought to be obtained by those skilled in the art utilizing the teachings disclosed herein.

Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof.

The invention claimed is:

1. A system for controlling a valve disposed in fluid communication with a fluid circuit, the system comprising:
- a flow sensor configured to determine a measured flow of fluid flowing from the fluid circuit to the valve;
- a pressure sensor configured to determine a measured pressure of fluid flowing from the fluid circuit to the valve; and
- an adaptive controller communicably coupled to the flow sensor and the pressure sensor, wherein the adaptive controller is configured to:
  - receive signals indicative of a target pressure, the measured flow, and the measured pressure;
  - determine a desired flow based at least on the measured pressure, the measured flow, and the target pressure;
  - determine a flow error as a difference between the desired flow and the measured flow; and
  - determine a desired position of the valve based on the flow error, such that the flow error is reduced;
- a position controller communicably coupled to the adaptive controller, wherein the position controller is configured to determine an actuating electric parameter based at least on the desired position of the valve; and
- a valve actuator communicably coupled to the position controller and the valve, wherein the valve actuator is configured to apply an actuating force on the valve based at least on the actuating electric parameter.

2. The system of claim 1, wherein the adaptive controller is further configured to:
- determine, via a reference model, a model pressure based on the target pressure;
- determine a pressure error as a difference between the measured pressure and the model pressure;
- determine, via an adaptive control model, a first gain and a second gain based on the target pressure, the measured pressure, and the pressure error;
- determine a first product as a product of the first gain and the target pressure;
- determine a second product as a product of the second gain and the measured pressure; and
- determine an adaptive error as a difference between the first product and the second product.

3. The system of claim 2, wherein the adaptive controller is further configured to:
- determine, via a dynamic estimator, an estimated resistance, and an estimated compliance based on the measured pressure and the measured flow, wherein each of the estimated resistance and the estimated compliance corresponds to an object disposed in fluid communication with the fluid circuit;
- receive a signal indicative of a tubing compliance of the fluid circuit; and
- determine, via an adaptive lag compensator, the desired flow based on the estimated resistance, the estimated compliance, the tubing compliance, and the adaptive error.

4. The system of claim 1, further comprising a position sensor communicably coupled to the position controller and configured to determine a measured position of the valve, wherein the position controller is further configured to:
- receive a signal indicative of a bias position of the valve;
- determine a position sum as a sum of the desired position and the bias position;
- determine a position error as a difference between the position sum and the measured position;
- determine a desired electric parameter by applying a first lead-lag compensator and a first limiter on the position error, wherein the first limiter is configured to limit the desired electric parameter within a first maximum limit;
- receive a feedback signal from the valve actuator, wherein the feedback signal is indicative of the actuating electric parameter;
- determine a controlling parameter error as a difference between the desired electric parameter and the feedback signal; and
- determine a controlling electric parameter by applying a second lead-lag compensator and a second limiter on the controlling parameter error, wherein the second limiter is configured to limit the controlling electric parameter within a second maximum limit.

5. The system of claim 4, wherein the position controller is further configured to:
- receive signals indicative of a desired maximum pressure, an effective cross-sectional area of a valve seat associated with the valve, and a force constant of the valve actuator; and
- determine the first maximum limit based on the desired maximum pressure, the effective cross-sectional area, and the force constant.

6. The system of claim 4, wherein the valve actuator is further configured to:
- determine an actuating parameter error based at least on a difference between the controlling electric parameter determined by the position controller and the actuating electric parameter; and
- apply the actuating force on the valve based on the actuating parameter error.

7. A method for controlling a valve disposed in fluid communication with a fluid circuit, the method comprising:

determining a measured flow of fluid flowing from the fluid circuit to the valve;

determining a measured pressure of fluid flowing from the fluid circuit to the valve;

determining a desired flow based at least on the measured pressure, the measured flow, and a target pressure;

determining a flow error as a difference between the desired flow and the measured flow;

determining a desired position of the valve based on the flow error, such that the flow error is reduced;

determining an actuating electric parameter based at least on the desired position of the valve; and applying an actuating force on the valve based at least on the actuating electric parameter.

8. The method of claim 7, wherein determining the desired flow further comprises:

determining, via a reference model, a model pressure based on the target pressure;

determining a pressure error as a difference between the measured pressure and the model pressure;

determining, via an adaptive control model, a first gain and a second gain based on the target pressure, the measured pressure, and the pressure error;

determining a first product as a product of the first gain and the target pressure;

determining a second product as a product of the second gain and the measured pressure; and determining an adaptive error as a difference between the first product and the second product.

9. The method of claim 8, wherein determining the desired flow further comprises:

determining, via a dynamic estimator, an estimated resistance, and an estimated compliance based on the measured pressure and the measured flow, wherein each of the estimated resistance and the estimated compliance corresponds to an object disposed in fluid communication with the fluid circuit;

receiving a signal indicative of a tubing compliance of the fluid circuit; and determining, via an adaptive lag compensator, the desired flow based on the estimated resistance, the estimated compliance, the tubing compliance, and the adaptive error.

10. The method of claim 7, wherein determining the actuating electric parameter further comprises:

determining a measured position of the valve;

receiving a signal indicative of a bias position of the valve;

determining a position sum as a sum of the desired position and the bias position;

determining a position error as a difference between the position sum and the measured position;

determining a desired electric parameter by applying a first lead-lag compensator and a first limiter on the position error, wherein the first limiter is configured to limit the desired electric parameter within a first maximum limit;

receiving a feedback signal indicative of the actuating electric parameter;

determining a controlling parameter error as a difference between the desired electric parameter and the feedback signal; and determining a controlling electric parameter by applying a second lead-lag compensator and a second limiter on the controlling parameter error, wherein the second limiter is configured to limit the controlling electric parameter within a second maximum limit.

11. The method of claim 10, further comprising:

receiving signals indicative of a desired maximum pressure, an effective cross-sectional area of a valve seat associated with the valve, and a force constant of the valve actuator configured to apply the actuating force on the valve; and determining the first maximum limit based on the desired maximum pressure, the effective cross-sectional area, and the force constant.

12. The method of claim 10, wherein applying the actuating force further comprises:

determining an actuating parameter error based at least on a difference between the controlling electric parameter and the actuating electric parameter; and applying the actuating force on the valve based on the actuating parameter error.

13. A valve system for use with a fluid circuit, the valve system comprising:

a valve comprising:

a valve housing defining an inlet port disposed in fluid communication with the fluid circuit and an exhaust port disposed in fluid communication with an environment external to the valve; and a valve body at least partially received within the valve housing and movable relative to the valve housing, wherein the valve body is configured to control fluid flow between the inlet port and the exhaust port;

a flow sensor configured to determine a measured flow of fluid flowing from the fluid circuit to the inlet port of the valve;

a pressure sensor configured to determine a measured pressure of fluid flowing from the fluid circuit to the inlet port of the valve;

an adaptive controller communicably coupled to the flow sensor and the pressure sensor, wherein the adaptive controller is configured to:

receive signals indicative of a target pressure, the measured flow, and the measured pressure;

determine a desired flow based at least on the measured pressure, the measured flow, and the target pressure;

determine a flow error as a difference between the desired flow and the measured flow; and determine a desired position of the valve body based on the flow error, such that the flow error is reduced;

a position controller communicably coupled to the adaptive controller, wherein the position controller is configured to determine an actuating electric parameter based at least on the desired position of the valve body; and a valve actuator communicably coupled to the position controller, wherein the valve actuator is configured to apply an actuating force on the valve body based at least on the actuating electric parameter in order to control fluid flow from the inlet port to the exhaust port.

14. The valve system of claim 13, wherein the adaptive controller is further configured to:

determine, via a reference model, a model pressure based on the target pressure;

determine a pressure error as a difference between the measured pressure and the model pressure;

determine, via an adaptive control model, a first gain and a second gain based on the target pressure, the measured pressure, and the pressure error;

determine a first product as a product of the first gain and the target pressure;

determine a second product as a product of the second gain and the measured pressure; and determine an adaptive error as a difference between the first product and the second product.

15. The valve system of claim 14, wherein the adaptive controller is further configured to:

determine, via a dynamic estimator, an estimated resistance, and an estimated compliance based on the measured pressure and the measured flow, wherein each of the estimated resistance and the estimated compliance corresponds to an object disposed in fluid communication with the fluid circuit;

receive a signal indicative of a tubing compliance of the fluid circuit; and determine, via an adaptive lag compensator, the desired flow based on the estimated resistance, the estimated compliance, the tubing compliance, and the adaptive error.

16. The valve system of claim 13, further comprising a position sensor communicably coupled to the position controller and configured to determine a measured position of the valve body relative to the valve housing, wherein the position controller is further configured to:

receive a signal indicative of a bias position of the valve body;

determine a position sum as a sum of the desired position and the bias position;

determine a position error as a difference between the position sum and the measured position;

determine a desired electric parameter by applying a first lead-lag compensator and a first limiter on the position error, wherein the first limiter is configured to limit the desired electric parameter within a first maximum limit;

receive a feedback signal from the valve actuator, wherein the feedback signal is indicative of the actuating electric parameter;

determine a controlling parameter error as a difference between the desired electric parameter and the feedback signal; and determine a controlling electric parameter by applying a second lead-lag compensator and a second limiter on the controlling parameter error, wherein the second limiter is configured to limit the controlling electric parameter within a second maximum limit.

17. The valve system of claim 13, wherein the valve further comprises a valve seat disposed adjacent to the inlet port and a membrane coupled to the valve housing and configured to selectively engage with the valve seat to close the inlet port, wherein the valve body comprises a disc coupled to the membrane and a stem extending from the disc along a longitudinal axis, and wherein the valve body is configured to move the membrane along the longitudinal axis based on the actuating force applied by the valve actuator on the stem.

18. The valve system of claim 17, wherein the valve actuator comprises:

a stator comprising a permanent magnet;

a coil coupled to the stem of the valve body, wherein the coil is configured to apply the actuating force on the stem based on the actuating electric parameter in order to move the stem along the longitudinal axis; and a spring engaged with the valve body and configured to bias the valve body away from the valve seat.

19. The valve system of claim 13, wherein the valve body is rotatable relative to the valve housing about a rotational axis, the valve body defining a body port therethrough, wherein a rotation of the valve body relative to the valve housing controls a degree of overlap between the body port and at least one of the inlet port and the exhaust port, and wherein the valve actuator is configured to apply the actuating force on the valve body in order to rotate the valve body relative to the valve housing.

20. A ventilator for use with a patient, the ventilator comprising:

a patient circuit comprising an inspiratory limb configured to supply breathable gas to the patient and an expiratory limb configured to receive exhaled gas from the patient; and the valve system of claim 13, wherein the inlet port of the valve is disposed in fluid communication with the expiratory limb of the patient circuit, and wherein the valve is configured to discharge the exhaled gas to the environment external to the valve.

* * * * *